:# (12) United States Patent
Suzuki

(10) Patent No.: US 11,813,303 B2
(45) Date of Patent: Nov. 14, 2023

(54) HOT FLASH AMELIORANT

(71) Applicant: KAO CORPORATION, Tokyo (JP)

(72) Inventor: Atsushi Suzuki, Shimotsuke (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/753,153

(22) PCT Filed: Oct. 3, 2018

(86) PCT No.: PCT/JP2018/037046
§ 371 (c)(1),
(2) Date: Apr. 2, 2020

(87) PCT Pub. No.: WO2019/069981
PCT Pub. Date: Apr. 11, 2019

(65) Prior Publication Data
US 2020/0237845 A1 Jul. 30, 2020

(30) Foreign Application Priority Data
Oct. 3, 2017 (JP) .................. 2017-193174

(51) Int. Cl.
*A61K 36/74* (2006.01)
*A61P 15/12* (2006.01)
*A61K 9/00* (2006.01)
*A61K 31/235* (2006.01)

(52) U.S. Cl.
CPC ............ *A61K 36/74* (2013.01); *A61K 9/0053* (2013.01); *A61K 31/235* (2013.01); *A61P 15/12* (2018.01)

(58) Field of Classification Search
CPC .... A61K 36/74; A61K 9/0053; A61K 31/235; A61P 15/12
See application file for complete search history.

(56) References Cited

FOREIGN PATENT DOCUMENTS

| CN | 101120936 A | | 2/2008 |
| CN | 104686764 A | | 6/2015 |
| JP | 2002-145765 A | | 5/2002 |
| JP | 2006-174746 A | | 7/2006 |
| JP | 2010-187554 A | | 9/2010 |
| JP | 66307329 | * | 4/2018 |
| JP | 2019-85361 A | | 6/2019 |

OTHER PUBLICATIONS

Smith (2011).*
David The british Medical Journal (1998) 727-729.*
International Search Report dated Dec. 18, 2018 in PCT/JP2018/037046 filed on Oct. 3, 2018, 2 pages.
Berendsen, "The role of serotonin in hot flushes", Maturitas, 2000, vol. 36, pp. 155-164.
QLifePro, Medical News, section "Relaxing with coffee", 2014, online, <http://www.qlifepro.com/news/20140822/menopause-and-the-coffee-better-with-love.html>, 4 total pages (with unedited computer-generated English translation).
Ochiai et al, "Effect of chlorogenic acids on fatigue and sleep in healthy males: A randomized, double-blind, placebo-controlled, crossover study", Food Sci Nutr., (2018), vol. 6, pp. 2530-2536.
Park et al, "Effects of subacute ingestion of chlorogenic acids on sleep architecture and energy metabolism through activity of the autonomic nervous system: a randomized, placebo-controlled, double-blinded cross-over trial", British Journal of Nutrition, (2017), vol. 117, pp. 979-984.

* cited by examiner

*Primary Examiner* — Shirley V Gembeh
(74) *Attorney, Agent, or Firm* — Oblon, McClelland, Maier & Neustadt, L.L.P.

(57) ABSTRACT

To provide a material for improvement in a climacteric symptom such as hot flash. An oral hot flash improvement agent comprising chlorogenic acids as an active ingredient. An oral hot flash improvement agent comprising a coffee bean extract which comprises chlorogenic acids and in which a mass ratio of caffeine/chlorogenic acids is 0.015 or less, as an active ingredient.

6 Claims, 1 Drawing Sheet

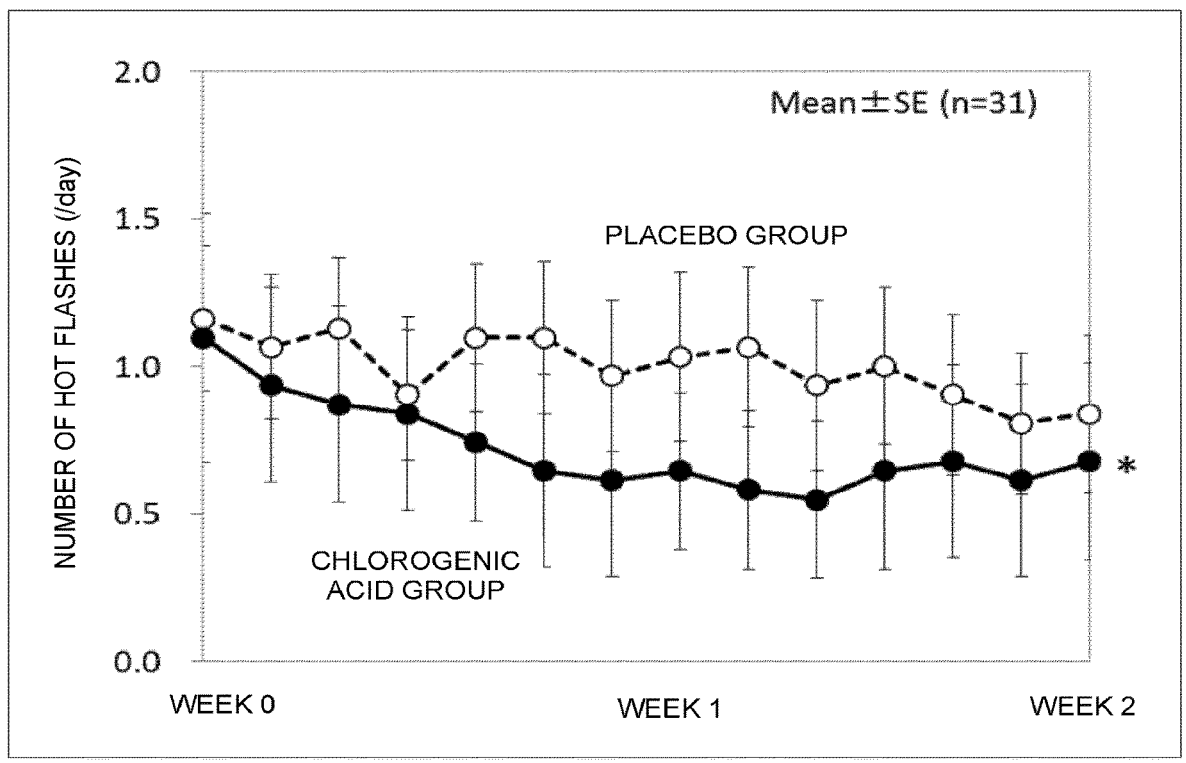

HOT FLASH AMELIORANT

FIELD OF THE INVENTION

The present invention relates to an agent for improving hot flash as one climacteric symptom.

BACKGROUND OF THE INVENTION

Climacteric symptoms and climacteric disorders are somatic disorders caused due to violent variation and/or reduction in secretion of sex hormones. Various symptoms appear in the climacterium, for example, palpitation, sweating, hot flash (flushing or flush), a feeling of cold, shoulder stiffness, backache, headache, insomnia, and depressed feeling. In particular, hot flash is one representative climacteric symptom. Hormone replacement therapies for hormone replacement with estrogen or the like are conducted for climacteric disorders with severe symptoms. Such hormone therapies, however, are feared to cause side effects such as an increase in the risk of cancer, and thus various symptoms in the climacterium are demanded to be more safely improved.

Chlorogenic acids is one polyphenol found in green coffee beans. Such chlorogenic acids has been heretofore reported to exert physiological activities such as an effect of improving an autonomic nerve function and an effect of improving indefinite complaint (Patent Literature 1). On the contrary, coffee and caffeine have been reported to have an effect of inducing hot flash (Non Patent Literature 1).

(Patent Literature 1) JP-A-2002-145765
(Non Patent Literature 1) Maturitas, 2,000, 36 (3): 155-64

SUMMARY OF THE INVENTION

Accordingly, the present invention provides an oral hot flash improvement agent comprising chlorogenic acids as an active ingredient.

The present invention also provides an oral hot flash improvement agent comprising a coffee bean extract which comprises chlorogenic acids and in which a mass ratio of caffeine/chlorogenic acids is 0.015 or less, as an active ingredient.

The present invention further provides a food product for improvement in hot flash, comprising chlorogenic acids as an active ingredient.

The present invention further provides a food product for improvement in hot flash, comprising a coffee bean extract which comprises chlorogenic acids and in which a mass ratio of caffeine/chlorogenic acids is 0.015 or less, as an active ingredient.

BRIEF DESCRIPTION OF THE DRAWINGS

FIG. 1 illustrates the change in the number of hot flashes per day during a testing period. *: There is significant difference within a significance level of 5% relative to a placebo group (ANOVA).

DETAILED DESCRIPTION OF THE INVENTION

The present invention relates to provision of a material for improvement in a climacteric symptom.

The present inventors have intensive studies, and as a result, found that ingestion of a coffee bean extract comprising chlorogenic acids is effective for improvement in a climacteric symptom such as hot flash.

According to the present invention, improvement in a climacteric symptom can be achieved without any concern about a side effect such as an increase in the risk of cancer as in a hormone therapy.

The Japan Society of Obstetrics and Gynecology defines climacteric symptoms and climacteric disorders as follows: five years around the menopause are called the climacterium, symptoms not caused by any organic changes, among a wide variety of symptoms appearing in such a period, are called climacteric symptoms, and clinical conditions interfering with daily life, among such climacteric symptoms, are called climacteric disorders" (Josei Igaku Guidebook Konenki Iryo Hen 2014 Nendo Ban, Nippon Josei Igaku Gakkai (The Japan Society for Menopause and Women's Health) Hen). Examples of climacteric symptoms include palpitation, sweating, hot flash, cold limbs shoulder and/or neck stiffness, backache, headache, insomnia, depressed feeling, excitation/grumpiness, fatigability, eyestrain, forgetfulness, dizziness, and joint ache. The phrase "improvement in a climacteric symptom" herein refers to improvement in any climacteric symptom listed above, preferably improvement in hot flash.

The term "hot flash" herein refers to any symptom of a feeling of heat and sweating occurring in the head or the chest or throughout the body, which is suddenly experienced during the climacterium.

The term "improvement" herein refers to amelioration of any disease, symptom or condition, prevention, suppression or retardation of exacerbation of any disease, symptom or condition, or reversion, prevention, suppression or retardation of progression of any disease, symptom or condition.

The term "chlorogenic acids" herein is a collective term of monocaffeoylquinic acids including 3-caffeoylquinic acid, 4-caffeoylquinic acid and 5-caffeoylquinic acid, monoferuloylquinic acids including 3-feruloylquinic acid, 4-feruloylquinic acid and 5-feruloylquinic acid, and dicaffeoylquinic acids including 3,4-dicaffeoylquinic acid, 3,5-dicaffeoylquinic acid and 4,5-dicaffeoylquinic acid. The chlorogenic acids for use as an active ingredient in the present invention or the chlorogenic acids comprised in the coffee bean extract for use as an active ingredient in the present invention is preferably at least one selected from the group consisting of 3-caffeoylquinic acid, 4-caffeoylquinic acid, 5-caffeoylquinic acid, 3-feruloylquinic acid, 4-feruloylquinic acid, 5-feruloylquinic acid, 3,4-dicaffeoylquinic acid, 3,5-dicaffeoylquinic acid and 4,5-dicaffeoylquinic acid, more preferably at least one selected from the group consisting of 3-caffeoylquinic acid, 4-caffeoylquinic acid, 5-caffeoylquinic acid, 3-feruloylquinic acid, 4-feruloylquinic acid and 5-feruloylquinic acid, further preferably at least one selected from the group consisting of 3-caffeoylquinic acid, 4-caffeoylquinic acid and 5-caffeoylquinic acid, more further preferably 3-caffeoylquinic acid, 4-caffeoylquinic acid and 5-caffeoylquinic acid, more further preferably, 3-caffeoylquinic acid, 4-caffeoylquinic acid, 5-caffeoylquinic acid, 3-feruloylquinic acid, 4-feruloylquinic acid and 5-feruloylquinic acid, more further preferably, 3-caffeoylquinic acid, 4-caffeoylquinic acid, 5-caffeoylquinic acid, 3-feruloylquinic acid, 4-feruloylquinic acid, 5-feruloylquinic acid, 3,4-dicaffeoylquinic acid, 3,5-dicaffeoylquinic acid and 4,5-dicaffeoylquinic acid. The chlorogenic acids includes stereoisomer and analog thereof, and a pure stereoisomer or analog, or a mixture thereof.

The chlorogenic acids described above may be in the form of a salt. Such a salt is preferably a pharmaceutically acceptable salt. Such a salt here used is, for example, a salt with an alkali metal such as lithium, sodium or potassium; a salt with an alkali earth metal such as magnesium or calcium; a salt of an inorganic base, such as an ammonium salt; a salt with a basic amino acid such as arginine, lysine, histidine or ornithine; or a salt with an organic base such as monoethanolamine, diethanolamine or triethanolamine. In particular, a salt with an alkali metal or alkali earth metal is preferable.

In one aspect of the present invention, the chlorogenic acids is used as an active ingredient for improvement in a climacteric symptom. In another aspect of the present invention, a coffee bean extract which comprises the chlorogenic acids and in which the mass ratio of caffeine/chlorogenic acids is 0.015 or less (in other words, the mass ratio of chlorogenic acids/caffeine is 65 or more) is comprised as an active ingredient for improvement in a climacteric symptom. The phrase "coffee bean extract which comprises the chlorogenic acids and in which the mass ratio of caffeine/chlorogenic acids is 0.015 or less" may be herein simply referred to as "coffee bean extract".

The content of the chlorogenic acids in the total amount of the coffee bean extract for use in the present invention is preferably 10% by mass or more, more preferably 15% by mass or more, and preferably 70% by mass or less, more preferably 60% by mass or less in terms of a physiological effect. The content of the chlorogenic acids in the coffee bean extract is herein based on the total amount of the above nine compounds (3-caffeoylquinic acid, 4-caffeoylquinic acid, 5-caffeoylquinic acid, 3-feruloylquinic acid, 4-feruloylquinic acid, 5-feruloylquinic acid, 3,4-dicaffeoylquinic acid, 3,5-dicaffeoylquinic acid and 4,5-dicaffeoylquinic acid). When caffeoylquinic acids and feruloylquinic acids (3-caffeoylquinic acid, 4-caffeoylquinic acid, 5-caffeoylquinic acid, 3-feruloylquinic acid, 4-feruloylquinic acid and 5-feruloylquinic acid) are used as chlorogenic acid, the content of the chlorogenic acid compound in the coffee bean extract is prescribed based on the total amount of such caffeoylquinic acids and feruloylquinic acids. In the case of use of caffeoylquinic acids (3-caffeoylquinic acid, 4-caffeoylquinic acid and 5-caffeoylquinic acid) for chlorogenic acid, the content of the chlorogenic acid in the coffee bean extract is prescribed based on the total amount of such caffeoylquinic acids.

The coffee bean extract for use in the present invention is preferably decaffeinated. The mass ratio of caffeine/chlorogenic acids in such a decaffeinated coffee bean extract may be 0.015 or less, and the ratio is preferably 0.014 or less, more preferably 0.010 or less, further preferably 0.0066 or less, further preferably 0.0050 or less, further preferably 0.0020 or less, further preferably 0.0005 or less from the viewpoint of the effect of improvement in a climacteric symptom such as hot flash. In other words, the mass ratio of chlorogenic acids/caffeine in the decaffeinated coffee bean extract may be 65 or more, and the ratio is preferably 70 or more, more preferably 100 or more, further preferably 150 or more, further preferably 200 or more, further preferably 500 or more, further preferably 2,000 or more from the viewpoint of the effect of improvement in a climacteric symptom such as hot flash. The content of caffeine in the coffee bean extract for use in the present invention, in the total amount thereof, is preferably 0.5% by mass or less, more preferably 0.4% by mass or less, further preferably 0.3% by mass or less, further preferably 0.2% by mass or less, further preferably 0.15% by mass or less, further preferably 0.1% by mass or less, further preferably 0.05% by mass or less, in terms of a physiological effect, and the coffee bean extract still preferably comprises substantially no caffeine.

Analysis of the chlorogenic acids and caffeine in the coffee bean extract is made according to a method described in Examples below. The contents of the chlorogenic acids and caffeine in the coffee bean extract are herein defined as the respective mass rates thereof relative to the solid content of the coffee bean extract. The term "solid content" herein refers to the balance obtained by removal of volatile matter with drying of a sample in an electric constant-temperature dryer at 105° C. for 3 hours.

The chlorogenic acids for use in the present invention can be extracted from a coffee bean. The coffee bean extract for use in the present invention can be obtained by subjecting a coffee bean to an extraction process. It is known that significant amounts of chlorogenic acids abundantly included in green coffee beans are lost by roasting. Thus, the coffee bean serving as a raw material of the chlorogenic acids and the coffee bean extract for use in the present invention is preferably a green coffee bean before roasting, and may be a lightly roasted coffee bean low in the degree of roasting. Hereinafter, the green coffee bean and the lightly roasted coffee bean may be simply referred to as "coffee bean".

The L value of the lightly roasted coffee bean is preferably 27 or more, more preferably 29 or more, further preferably 35 or more from the viewpoint of the content or the like of the chlorogenic acids, and is preferably less than 62, more preferably 60 or less, further preferably 55 or less from the viewpoint of taste. The L value of the lightly roasted coffee bean is preferably in the range of 27 or more and less than 62, more preferably 29 or more and 60 or less, further preferably 35 or more and 55 or less. The term "L value" is herein determined by measuring the color value of a roasted coffee bean after grinding, with a colorimeter (for example, spectrophotometer SE 2000 manufactured by Nippon Denshoku Industries Co., Ltd.), under the assumption that the L value of black is 0 and the L value of white is 100.

The chlorogenic acids and the coffee bean extract can be extracted from the coffee bean by use of hot water. The coffee bean to be subjected to extraction may be any coffee bean not ground or ground. Any known method and apparatus, for example, a grinding apparatus such as a cutter mill, a hammer mill, a jet mill, an impact mill or a wiley grinder can be used for grinding of the coffee bean, and a method therefor is not particularly limited. The average grain size of the coffee bean ground can be appropriately selected. Such extraction can be performed by a known method such as batch extraction, drip extraction or column extraction. The extraction method here adopted can be, for example, any method described in JP-A-S58-138347, JP-A-S59-51763, JP-A-S62-111671, or JP-A-H05-236918. The extraction process can provide an extraction liquid of the coffee bean.

The extraction liquid of the coffee bean, obtained by the extraction, may be, if necessary, concentrated or dried. Examples of a procedure for forming the extraction liquid into a dried product include lyophilization, evaporation to dryness, and spray drying. Examples of a procedure for forming the extraction liquid into a concentered product include concentration under reduced pressure and reverse osmosis membrane concentration. The concentrated product of the extraction liquid refers to one obtained by at least partially removing a solvent from the extraction liquid of the coffee bean to thereby increase the concentration of the chlorogenic acids. Examples of the form of the concentrated product include various forms such as a solid, a liquid and a slurry.

Alternatively, the chlorogenic acids for use in the present invention can also be extracted from a plant comprising chlorogenic acids, other than coffee. Examples of such a plant include cabbage, lettuce, artichoke, tomato, eggplant, potato, carrot, apple, pear, plum, Japanese plum fruit, peach, apricot, cherry, sunflower, mulukhiya, sugar cane, nandina leaf, blueberry, and wheat. The chlorogenic acids for use in the present invention can be preferably extracted from a green coffee bean, a lightly roasted coffee bean, a nandina leaf, an unripe fruit of an apple, a sunflower seed, a Japanese plum fruit, or the like. Alternatively, a commercially available green coffee bean extract, apple extract or sunflower seed extract can be used for the chlorogenic acids in the present invention.

Examples of a procedure for selectively reducing caffeine in the coffee bean extract include a method including subjecting the decaffeinated coffee bean to an extraction process, and a method including subjecting the extraction liquid of the coffee bean or the concentrated product thereof to a decaffeination treatment. In particular, a method including subjecting the extraction liquid of the coffee bean or the concentrated product thereof to a decaffeination treatment is preferable. The decaffeination treatment of the extraction liquid of the coffee bean or the concentrated product thereof is preferably conducted by bringing the extraction liquid of the coffee bean or the concentrated product thereof, which is dissolved in a mixed solution of water and an organic solvent, into contact with activated carbon and/or activated earth or acid earth. For example, any method described in JP-A-2011-4766 can be adopted. A commercially available product may also be used for the extraction liquid of the coffee bean or the concentrated product thereof to be subjected to the decaffeination treatment. The decaffeinated coffee bean is any coffee bean subjected to the decaffeination treatment. A known method can be adopted for the decaffeination treatment of the coffee bean, and examples thereof include a water method, a supercritical carbon dioxide extraction method, and an organic solvent extraction method.

The chlorogenic acids for use in the present invention or the coffee bean extract for use in the present invention can be prepared according to the foregoing procedure. The chlorogenic acids or the coffee bean extract prepared can be in the form of a solid, a liquid, a dried product, a slurry, or the like.

As shown in Examples described below, hot flash as one climacteric symptom has been improved by oral ingestion of the coffee bean extract. Accordingly, the coffee bean extract or the chlorogenic acids can be used for improvement in a climacteric symptom such as hot flash, with being orally administered or orally ingested.

Accordingly, in one aspect, the present invention provides an oral climacteric symptom improvement agent. In one embodiment, the climacteric symptom improvement agent of the present invention comprises chlorogenic acids as an active ingredient. In another embodiment, the climacteric symptom improvement agent of the present invention comprises a coffee bean extract as an active ingredient. In another aspect, the present invention provides use of chlorogenic acids or a coffee bean extract for production of an oral climacteric symptom improvement agent. The oral climacteric symptom improvement agent, when orally administered to or orally ingested by an individual, exerts the effect of improving climacteric symptom, for example, exhibits improvement in hot flash. In a preferable embodiment, the climacteric symptom improvement agent is a hot flash improvement agent.

In one embodiment, the oral climacteric symptom improvement agent is essentially configured from the chlorogenic acids or the coffee bean extract. In another embodiment, the oral climacteric symptom improvement agent can be an oral composition comprising at least the chlorogenic acids or the coffee bean extract. Examples of the composition include a pharmaceutical product and a quasi-drug which can be orally administered, and a food product, described below.

In another aspect, the present invention provides use of the chlorogenic acids or the coffee bean extract for improvement in a climacteric symptom. In still another aspect, the present invention provides the chlorogenic acids or the coffee bean extract for use in improvement in a climacteric symptom. The chlorogenic acids or the coffee bean extract is orally administered or orally ingested. In a preferable embodiment, the improvement in a climacteric symptom is improvement in hot flash. The use according to the present invention may be therapeutic use or non-therapeutic use. Examples of such therapeutic use include use in a subject in need of a therapy of or improvement in a climacteric symptom interfering with daily life, preferably a therapy of or improvement in a climacteric disorder. Examples of such non-therapeutic use include use in a subject in need of improvement in a climacteric symptom not interfering with daily life. The term "non-therapeutic" is a concept including no medical practices, namely, a concept including no method of operating, treating or diagnosing a human being, more specifically a concept including no method of operating, treating or diagnosing a human being by a doctor or a person who receives an instruction from a doctor.

In the present invention, the chlorogenic acids or the coffee bean extract can be used for both a human and a non-human animal, and preferably used for a human, more preferably used for a climacteric human, further preferably a climacteric female, further preferably a climacteric female having a symptom of hot flash, further preferably a climacteric female having a symptom of hot flash twice or more a week on average, further preferably a climacteric female having a symptom of hot flash four times or more a week on average, further preferably a climacteric female having a symptom of hot flash seven times or more a week on average.

In the present invention, the chlorogenic acids or the coffee bean extract can be used in a pharmaceutical product, a quasi-drug or a food product (encompassing a food product for a non-human animal), as an active ingredient for imparting a function of improving a climacteric symptom.

The pharmaceutical product (also encompassing the quasi-drug) is a pharmaceutical product for improvement in a climacteric symptom (preferably improvement in hot flash), and comprises the chlorogenic acids or the coffee bean extract as the active ingredient for the function. The pharmaceutical product may further include, if necessary, a pharmaceutically acceptable carrier, or other active ingredient, a pharmacological ingredient or the like as long as the function of the active ingredient is not impaired.

The pharmaceutical product (also encompassing the quasi-drug) is orally administered. Examples of the dosage form of the pharmaceutical product include a dosage form which can be orally administered, for example, oral solid formulations such as a tablet (encompassing a chewable tablet and the like), a capsule, a granule, a powder and a troche, and oral liquid formulations such as an internal liquid and a syrup. A formulation of such a dosage form can be prepared by appropriately combining the chlorogenic acids or the coffee bean extract with a pharmaceutically acceptable carrier (for example, an excipient, a binder, an extender, a disintegrant, a surfactant, a lubricant, a dispersant, a buffer, a preservative, a corrigent, a flavoring agent, a coating, or a diluent), other medicinal ingredients, or the like, according to an ordinary method.

The food product is a food product for improvement in climacteric symptom (preferably improvement in hot flash), and comprises the chlorogenic acids or the coffee bean extract as the active ingredient for the function. The food product has a concept of improvement in climacteric symptom (preferably improvement in hot flash), and encompasses a food product for the sick, and foods with health claims, such as a food with nutrient function claims, a food for specified health use, and a food with functional claims, on which the above concept is, if necessary, labeled.

The food product provided by the present invention encompasses a drink. Accordingly, the food product can be put into a food and drink product. The form of the food product can be a solid, a semi-solid or a liquid (for example, a drink). Examples of the food product include drinks such as a cooling drink, a tea drink, a coffee drink, a fruit juice drink, a carbonated drink, a jelly-like drink and near-water, food and drink products such as jelly, wafer, biscuit, bread, noodle and sausage, various food products such as a nutritional food, and raw materials thereof. Alternatively, the food product may be a supplement in the form of an oral administration formulation, such as a tablet, a capsule, a granule, a powder, a liquid or a syrup. In particular, a drink is preferable.

The food product can be prepared by appropriately combining the chlorogenic acids or the coffee bean extract with any food product material or other active ingredient, or an additive acceptable in a food product (for example, a solvent, a softener, an oil, an emulsifier, a preservative agent, an acidulant, a sweetener, a bittering agent, a pH adjuster, a stabilizer, a coloring agent, an ultraviolet absorber, an antioxidant, a moisturizing agent, a thickener, a bonding agent, a dispersant, a fluidity improver, a wetting agent, a flavoring agent, a seasoning, or a flavor modifier), according to an ordinary method.

The oral liquid formulation or the drink may comprise at least one selected from the group consisting of water and ethanol, as a solvent. The proportion of such water in the solvent in the oral liquid formulation or the drink is not particularly limited, and is preferably 95% by mass or more, more preferably 97% by mass or more, particularly preferably 99.5% by mass or more, and preferably 100% by mass or less relative to the total amount of the solvent. Examples of such water include ion-exchange water, tap water, and spring water, and ion-exchange water is particularly preferable in terms of taste. The content of the solvent in the oral liquid formulation or the drink is preferably 85% by mass or more, preferably 90% by mass or more.

The content of the chlorogenic acids or the coffee bean extract in the pharmaceutical product, the quasi-drug or the food product can vary depending on the dosage form or the form. By way of example, the content of the coffee bean extract in a liquid composition (for example, oral liquid formulation or drink) in the total mass thereof, in terms of solid content of the coffee bean extract, is preferably 0.01% by mass or more, more preferably 0.05% by mass or more, further preferably 0.2% by mass or more, and preferably 10% by mass or less, more preferably 4% by mass or less, further preferably 2% by mass or less. By way of another example, the content of the chlorogenic acids in a liquid composition (for example, oral liquid formulation or drink) in the total mass thereof is preferably 0.001% by mass or more, more preferably 0.005% by mass or more, further preferably 0.02% by mass or more, and preferably 7% by mass or less, more preferably 3% by mass or less, further preferably 1.5% by mass or less. By way of still another example, the content of the coffee bean extract in a solid composition (for example, oral solid formulation, solid food product, or supplement) in the total mass thereof, in terms of solid content of the coffee bean extract, is preferably 0.1% by mass or more, more preferably 0.5% by mass or more, further preferably 2% by mass or more, and preferably 95% by mass or less, more preferably 90% by mass or less, further preferably 80% by mass or less. By way of still another example, the content of the chlorogenic acids in a solid composition (for example, oral solid formulation, solid food product, or supplement) in the total mass thereof is preferably 0.01% by mass or more, more preferably 0.05% by mass or more, further preferably 0.2% by mass or more, and preferably 70% by mass or less, more preferably 65% by mass or less, further preferably 60% by mass or less.

In still another aspect, the present invention provides a method for improving climacteric symptom in a subject. The method comprises orally administering an effective amount of the chlorogenic acids or the coffee bean extract to a subject. In a preferable embodiment, the improvement in climacteric symptom is improvement in hot flash. The method of the present invention may be a therapeutic method or a non-therapeutic method.

Examples of the subject in the method of the present invention include an animal in need of improvement in climacteric symptom, preferably improvement in hot flash. Examples of the animal include a human and a non-human animal, listed above, and the animal is more preferably a human. The human is preferably a climacteric human, more preferably a climacteric female, further preferably a climacteric female having a symptom of hot flash, further preferably a climacteric female having a symptom of hot flash twice or more a week on average, further preferably a climacteric female having a symptom of hot flash four times or more a week on average, further preferably a climacteric female having a symptom of hot flash seven times or more a week on average.

The effective amount administered in the method of the present invention can be an amount which enables improvement in a climacteric symptom of the subject to be achieved. The effective amount is preferably an amount which enables a climacteric symptom (preferably hot flash) in an administration group to be statistically significantly improved as compared with that in a non-administration group.

In the present invention, the dosage and the regimen of the chlorogenic acids or the coffee bean extract can be appropriately determined by those skilled in the art, depending on the species, the weight, the sex, the age, the condition or other factor of the subject. The dosage of the chlorogenic acids or the coffee bean extract in the present invention (in terms of chlorogenic acids) is, without limitation, for example, preferably 50 mg or more, more preferably 70 mg or more, further preferably 100 mg or more, and preferably 1500 mg or less, more preferably 1000 mg or less, further preferably 500 mg or less per adult per day. A preferable range of the dosage per adult per day in terms of chlorogenic acids is from 50 to 1500 mg, more preferably from 70 to 1,000 mg, further preferably from 100 to 500 mg. In the present invention, the above dosage of the chlorogenic acids or the coffee bean extract is preferably orally administered or orally ingested, for example, once per day or in a divided manner of twice, or three times or more per day, more preferably orally administered or orally ingested once per day. The period of administration or ingestion is not particularly limited, and is preferably successive, more preferably one week or more, further preferably two weeks or more, further preferably four weeks or more. The timing of administration or ingestion is preferably during the period from after dinner until bedtime, more preferably within 1 hour before bedtime.

In a preferable embodiment of the present invention, the above daily dosage of the chlorogenic acids or the coffee bean extract is orally administered to or orally ingested by a climacteric human in need of improvement in a climacteric symptom (preferably hot flash) within 1 hour before bedtime once per day for two weeks or more.

The present invention also encompasses the following substance, production method, use, method, and the like as exemplary embodiments, provided that the present invention is not limited to such embodiments.

[1] An oral climacteric symptom improvement agent comprising chlorogenic acids as an active ingredient.

[2] An oral climacteric symptom improvement agent comprising a coffee bean extract which comprises chlorogenic acids and in which a mass ratio of caffeine/chlorogenic acids is 0.015 or less, as an active ingredient.

[3] The oral climacteric symptom improvement agent according to [2], wherein the coffee bean extract is preferably a green coffee bean extract and/or a lightly roasted coffee bean extract.

[4] The oral climacteric symptom improvement agent according to [2] or [3], wherein the mass ratio of caffeine/chlorogenic acids is preferably 0.014 or less, more preferably 0.010 or less, further preferably 0.0066 or less, further preferably 0.0050 or less, further preferably 0.0020 or less, further preferably 0.0005 or less.

[5] The oral climacteric symptom improvement agent according to any one of [2] to [4], wherein the agent is preferably a liquid composition comprising 0.01% by mass or more and 10% by mass or less of the coffee bean extract in terms of solid content, or a solid composition comprising 0.1% by mass or more and 95% by mass or less of the coffee bean extract in terms of solid content.

[6] The oral climacteric symptom improvement agent according to any one of [2] to [5], wherein a content of caffeine in the coffee bean extract is preferably 0.5% by mass or less, more preferably 0.4% by mass or less, further preferably 0.3% by mass or less, further preferably 0.2% by mass or less, further preferably 0.15% by mass or less, further preferably 0.1% by mass or less, further preferably 0.05% by mass or less.

[7] The oral climacteric symptom improvement agent according to any one of [1] to [6], wherein the chlorogenic acids is preferably at least one selected from the group consisting of 3-caffeoylquinic acid, 4-caffeoylquinic acid, 5-caffeoylquinic acid, 3-feruloylquinic acid, 4-feruloylquinic acid, 5-feruloylquinic acid, 3,4-dicaffeoylquinic acid, 3,5-dicaffeoylquinic acid and 4,5-dicaffeoylquinic acid, more preferably at least one selected from the group consisting of 3-caffeoylquinic acid, 4-caffeoylquinic acid, 5-caffeoylquinic acid, 3-feruloylquinic acid, 4-feruloylquinic acid and 5-feruloylquinic acid, further preferably at least one selected from the group consisting of 3-caffeoylquinic acid, 4-caffeoylquinic acid and 5-caffeoylquinic acid, more further preferably 3-caffeoylquinic acid, 4-caffeoylquinic acid and 5-caffeoylquinic acid, more further preferably 3-caffeoylquinic acid, 4-caffeoylquinic acid, 5-caffeoylquinic acid, 3-feruloylquinic acid, 4-feruloylquinic acid and 5-feruloylquinic acid, more further preferably 3-caffeoylquinic acid, 4-caffeoylquinic acid, 5-caffeoylquinic acid, 3-feruloylquinic acid, 4-feruloylquinic acid, 5-feruloylquinic acid, 3,4-dicaffeoylquinic acid, 3,5-dicaffeoylquinic acid and 4,5-dicaffeoylquinic acid.

[8] The oral climacteric symptom improvement agent according to any one of [1] to [7], wherein the agent is preferably a liquid composition comprising 0.001% by mass or more and 7% by mass or less of the chlorogenic acids in a total mass, or a solid composition comprising 0.01% by mass or more and 70% by mass or less of the chlorogenic acids in a total mass.

[9] The oral climacteric symptom improvement agent according to any one of [1] to [8], wherein from 50 to 1500 mg per adult per day of the chlorogenic acids is preferably orally administered or orally ingested.

[10] The oral climacteric symptom improvement agent according to any one of [1] to [9], wherein the agent is preferably administered or ingested for one week or more, more preferably two weeks or more, further preferably four weeks or more.

[11] The oral climacteric symptom improvement agent according to any one of [1] to [10], wherein the agent is preferably administered or ingested during the period from after dinner until bedtime, more preferably within 1 hour before bedtime.

[12] The oral climacteric symptom improvement agent according to any one of [1] to [11], wherein the agent is preferably liquid.

[13] The oral climacteric symptom improvement agent according to any one of [1] to [12], wherein the agent is preferably a food product.

[14] The oral climacteric symptom improvement agent according to any one of [1] to [13], wherein the climacteric symptom is preferably hot flash.

[15] Use of chlorogenic acids for production of an oral climacteric symptom improvement agent.

[16] Use of a coffee bean extract which comprises chlorogenic acids and in which a mass ratio of caffeine/chlorogenic acids is 0.015 or less, for production of an oral climacteric symptom improvement agent.

[17] The use according to [16], wherein the coffee bean extract is preferably a green coffee bean extract and/or a lightly roasted coffee bean extract.

[18] The use according to [16] or [17], wherein the mass ratio of caffeine/chlorogenic acids is preferably 0.014 or less, more preferably 0.010 or less, further preferably 0.0066 or less, further preferably 0.0050 or less, further preferably 0.0020 or less, further preferably 0.0005 or less.

[19] The use according to any one of [16] to [18], wherein the oral climacteric symptom improvement agent is a liquid composition preferably comprising 0.01% by mass or more, more preferably 0.05% by mass or more, further preferably 0.2% by mass or more of the coffee bean extract in terms of solid content, or a solid composition preferably comprising 0.1% by mass or more, more preferably 0.5% by mass or more, further preferably 2% by mass or more of the coffee bean extract in terms of solid content.

[20] The use according to [19], wherein the oral climacteric symptom improvement agent is a liquid composition preferably comprising 10% by mass or less, more preferably 4% by mass or less, further preferably 2% by mass or less of the coffee bean extract in terms of solid content, or a solid composition preferably comprising 95% by mass or less, more preferably 90% by mass or less, further preferably 80% by mass or less of the coffee bean extract in terms of solid content.

[21] The use according to any one of [16] to [20], wherein a content of caffeine in the coffee bean extract is preferably 0.5% by mass or less, more preferably 0.4% by mass or less, further preferably 0.3% by mass or less, further preferably 0.2% by mass or less, further preferably 0.15% by mass or less, further preferably 0.1% by mass or less, further preferably 0.05% by mass or less.

[22] The use according to any one of [15] to [21], wherein the chlorogenic acids is
preferably at least one selected from the group consisting of 3-caffeoylquinic acid, 4-caffeoylquinic acid, 5-caffeoylquinic acid, 3-feruloylquinic acid, 4-feruloylquinic acid, 5-feruloylquinic acid, 3,4-dicaffeoylquinic acid, 3,5-dicaffeoylquinic acid and 4,5-dicaffeoylquinic acid,
more preferably at least one selected from the group consisting of 3-caffeoylquinic acid, 4-caffeoylquinic acid, 5-caffeoylquinic acid, 3-feruloylquinic acid, 4-feruloylquinic acid and 5-feruloylquinic acid,
further preferably at least one selected from the group consisting of 3-caffeoylquinic acid, 4-caffeoylquinic acid and 5-caffeoylquinic acid,
more further preferably 3-caffeoylquinic acid, 4-caffeoylquinic acid and 5-caffeoylquinic acid,
more further preferably 3-caffeoylquinic acid, 4-caffeoylquinic acid, 5-caffeoylquinic acid, 3-feruloylquinic acid, 4-feruloylquinic acid and 5-feruloylquinic acid,
more further preferably 3-caffeoylquinic acid, 4-caffeoylquinic acid, 5-caffeoylquinic acid, 3-feruloylquinic acid, 4-feruloylquinic acid, 5-feruloylquinic acid, 3,4-dicaffeoylquinic acid, 3,5-dicaffeoylquinic acid and 4,5-dicaffeoylquinic acid.

[23] The use according to any one of [15] to [22], wherein the oral climacteric symptom improvement agent is a liquid composition preferably 0.001% by mass or more, more preferably 0.005% by mass or more, further preferably 0.02% by mass or more of the chlorogenic acids in a total mass, or a solid composition preferably comprising 0.01% by mass or more, more preferably 0.05% by mass or more, further preferably 0.2% by mass or more of the chlorogenic acids in a total mass.

[24] The use according to [23], wherein the oral climacteric symptom improvement agent is a liquid composition preferably comprising 7% by mass or less, more preferably 3% by mass or less, further preferably 1.5% by mass or less of the chlorogenic acids in a total mass, or a solid composition preferably comprising 70% by mass or less, more preferably 65% by mass or less, further preferably 60% by mass or less of the chlorogenic acids in a total mass.

[25] The use according to any one of [15] to [24], wherein an amount of the oral climacteric symptom improvement agent administered or ingested per adult per day is preferably 50 mg or more, more preferably 70 mg or more, further preferably 100 mg or more as an amount of the chlorogenic acids.

[26] The use according to [25], wherein the amount of the oral climacteric symptom improvement agent administered or ingested per adult per day is preferably 1500 mg or less, more preferably 1000 mg or less, further preferably 500 mg or less as the amount of chlorogenic acids.

[27] The use according to any one of [15] to [26], wherein the oral climacteric symptom improvement agent is preferably administered or ingested for one week or more, more preferably two weeks or more, further preferably four weeks or more.

[28] The use according to any one of [15] to [27], wherein the oral climacteric symptom improvement agent is administered or ingested preferably during the period from after dinner until bedtime, more preferably within 1 hour before bedtime.

[29] The use according to any one of [15] to [28], wherein the oral climacteric symptom improvement agent is preferably liquid.

[30] The use according to any one of [15] to [29], wherein the oral climacteric symptom improvement agent is preferably a food product.

[31] The use according to any one of [15] to [30], wherein the climacteric symptom is preferably hot flash.

[32] Use of chlorogenic acids as an active ingredient for improvement in a climacteric symptom, in an oral composition.

[33] Use of an oral composition comprising chlorogenic acids, for improvement in a climacteric symptom.

[34] Use of a coffee bean extract which comprises chlorogenic acids and in which a mass ratio of caffeine/chlorogenic acids is 0.015 or less, as an active ingredient for improvement in a climacteric symptom, in an oral composition.

[35] Use of an oral composition comprising a coffee bean extract which comprises chlorogenic acids and in which a mass ratio of caffeine/chlorogenic acids is 0.015 or less, for improvement in a climacteric symptom.

[36] The use according to [34] or [35], wherein the coffee bean extract is preferably a green coffee bean extract and/or a lightly roasted coffee bean extract.

[37] The use according to any one of [34] to [36], wherein the mass ratio of caffeine/chlorogenic acids is preferably 0.014 or less, more preferably 0.010 or less, further preferably 0.0066 or less, further preferably 0.0050 or less, further preferably 0.0020 or less, further preferably 0.0005 or less.

[38] The use according to any one of [34] to [37], wherein the oral composition is preferably a liquid composition comprising from 0.01 to 10% by mass, from 0.01 to 4% by mass, from 0.01 to 2% by mass, from 0.05 to 10% by mass, from 0.05 to 4% by mass, from 0.05 to 2% by mass, from 0.2 to 10% by mass, from 0.2 to 4% by mass or from 0.2 to 2% by mass of the coffee bean extract in terms of solid content, or
a solid composition comprising from 0.1 to 95% by mass, from 0.1 to 90% by mass, from 0.1 to 80% by mass, from 0.5 to 95% by mass, from 0.5 to 90% by mass, from 0.5 to 80% by mass, from 2 to 95% by mass, from 2 to 90% by mass or from 2 to 80% by mass of the coffee bean extract in terms of solid content.

[39] The use according to any one of [34] to [38], wherein a content of caffeine in the coffee bean extract is preferably 0.5% by mass or less, more preferably 0.4% by mass or less, further preferably 0.3% by mass or less, further preferably 0.2% by mass or less, further preferably 0.15% by mass or less, further preferably 0.1% by mass or less, further preferably 0.05% by mass or less.

[40] The use according to any one of [32] to [39], wherein the chlorogenic acids is
preferably at least one selected from the group consisting of 3-caffeoylquinic acid, 4-caffeoylquinic acid, 5-caffeoylquinic acid, 3-feruloylquinic acid, 4-feruloylquinic acid, 5-feruloylquinic acid, 3,4-dicaffeoylquinic acid, 3,5-dicaffeoylquinic acid and 4,5-dicaffeoylquinic acid, more preferably at least one selected from the group consisting of 3-caffeoylquinic acid, 4-caffeoylquinic acid, 5-caffeoylquinic acid, 3-feruloylquinic acid, 4-feruloylquinic acid and 5-feruloylquinic acid, further preferably at least one selected from the group consisting of 3-caffeoylquinic acid, 4-caffeoylquinic acid and 5-caffeoylquinic acid, more further preferably 3-caffeoylquinic acid, 4-caffeoylquinic acid and 5-caffeoylquinic acid, more further preferably 3-caffeoylquinic acid, 4-caffeoylquinic acid, 5-caffeoylquinic acid, 3-feruloylquinic acid, 4-feruloylquinic acid and 5-feruloylquinic acid, more further preferably 3-caffeoylquinic acid, 4-caffeoylquinic acid, 5-caffeoylquinic acid, 3-feruloylquinic acid, 4-feruloylquinic acid, 5-feruloylquinic acid, 3,4-dicaffeoylquinic acid, 3,5-dicaffeoylquinic acid and 4,5-dicaffeoylquinic acid.

[41] The use according to any one of [32] to [40], wherein the oral composition is preferably a liquid composition comprising from 0.001 to 7% by mass, from 0.001 to 3% by mass, from 0.001 to 1.5% by mass, from 0.005 to 7% by mass, from 0.005 to 3% by mass, from 0.005 to 1.5% by mass, from 0.02 to 7% by mass, from 0.02 to 3% by mass or from 0.02 to 1.5% by mass of the chlorogenic acids in a total mass, or a solid composition comprising from 0.01 to 70% by mass, from 0.01 to 65% by mass, from 0.01 to 60% by mass, from 0.05 to 70% by mass, from 0.05 to 65% by mass, from 0.05 to 60% by mass, from 0.2 to 70% by mass, from 0.2 to 65% by mass or from 0.2 to 60% by mass of the chlorogenic acids in a total mass.

[42] The use according to any one of [32] to [41], wherein an amount of the oral composition administered or ingested per adult per day is preferably from 50 to 1500 mg, from 70 to 1500 mg, from 100 to 1500 mg, from 50 to 1,000 mg, from 70 to 1,000 mg, from 100 to 1,000 mg, from 50 to 500 mg, from 70 to 500 mg or from 100 to 500 mg as an amount of the chlorogenic acids.

[43] The use according to any one of [32] to [42], wherein the oral composition is preferably administered or ingested for one week or more, more preferably two weeks or more, further preferably four weeks or more.

[44] The use according to any one of [32] to [43], wherein the oral composition is preferably administered or ingested during the period from after dinner until bedtime.

[45] The use according to any one of [32] to [44], wherein the oral composition is preferably administered or ingested within 1 hour before bedtime.

[46] The use according to any one of [32] to [45], wherein the oral composition is preferably liquid.

[47] The use according to any one of [32] to [46], wherein the oral composition is preferably a food product.

[48] The use according to any one of [32] to [47], wherein the climacteric symptom is preferably hot flash.

[49] Chlorogenic acids for use as an active ingredient for improvement in a climacteric symptom, in an oral composition.

[50] An oral composition comprising chlorogenic acids to be used for improvement in a climacteric symptom.

[51] A coffee bean extract which comprises chlorogenic acids and in which a mass ratio of caffeine/chlorogenic acids is 0.015 or less, for use as an active ingredient for improvement in a climacteric symptom, in an oral composition.

[52] An oral composition comprising a coffee bean extract which comprises chlorogenic acids and in which a mass ratio of caffeine/chlorogenic acids is 0.015 or less, for use in improvement in a climacteric symptom.

[53] The coffee bean extract or the oral composition according to [51] or [52], wherein the coffee bean extract is preferably a green coffee bean extract and/or a lightly roasted coffee bean extract.

[54] The coffee bean extract or the oral composition according to any one of [51] to [53], wherein the mass ratio of caffeine/chlorogenic acids is preferably 0.014 or less, more preferably 0.010 or less, further preferably 0.0066 or less, further preferably 0.0050 or less, further preferably 0.0020 or less, further preferably 0.0005 or less.

[55] The coffee bean extract or the oral composition according to any one of [51] to [54], wherein the oral composition is preferably a liquid composition comprising from 0.01 to 10% by mass, from 0.01 to 4% by mass, from 0.01 to 2% by mass, from 0.05 to 10% by mass, from 0.05 to 4% by mass, from 0.05 to 2% by mass, from 0.2 to 10% by mass, from 0.2 to 4% by mass or from 0.2 to 2% by mass of the coffee bean extract in terms of solid content, or a solid composition comprising from 0.1 to 95% by mass, from 0.1 to 90% by mass, from 0.1 to 80% by mass, from 0.5 to 95% by mass, from 0.5 to 90% by mass, from 0.5 to 80% by mass, from 2 to 95% by mass, from 2 to 90% by mass or from 2 to 80% by mass of the coffee bean extract in terms of solid content.

[56] The coffee bean extract or the oral composition according to any one of [51] to [55], wherein a content of caffeine in the coffee bean extract is preferably 0.5% by mass or less, more preferably 0.4% by mass or less, further preferably 0.3% by mass or less, further preferably 0.2% by mass or less, further preferably 0.15% by mass or less, further preferably 0.1% by mass or less, further preferably 0.05% by mass or less.

[57] The chlorogenic acids, the coffee bean extract or the oral composition according to any one of [49] to [56], wherein the chlorogenic acids is preferably at least one selected from the group consisting of 3-caffeoylquinic acid, 4-caffeoylquinic acid, 5-caffeoylquinic acid, 3-feruloylquinic acid, 4-feruloylquinic acid, 5-feruloylquinic acid, 3,4-dicaffeoylquinic acid, 3,5-dicaffeoylquinic acid and 4,5-dicaffeoylquinic acid, more preferably at least one selected from the group consisting of 3-caffeoylquinic acid, 4-caffeoylquinic acid, 5-caffeoylquinic acid, 3-feruloylquinic acid, 4-feruloylquinic acid and 5-feruloylquinic acid, further preferably at least one selected from the group consisting of 3-caffeoylquinic acid, 4-caffeoylquinic acid and 5-caffeoylquinic acid, more further preferably 3-caffeoylquinic acid, 4-caffeoylquinic acid and 5-caffeoylquinic acid, more further preferably 3-caffeoylquinic acid, 4-caffeoylquinic acid, 5-caffeoylquinic acid, 3-feruloylquinic acid, 4-feruloylquinic acid and 5-feruloylquinic acid, more further preferably 3-caffeoylquinic acid, 4-caffeoylquinic acid, 5-caffeoylquinic acid, 3-feruloylquinic acid, 4-feruloylquinic acid, 5-feruloylquinic acid, 3,4-dicaffeoylquinic acid, 3,5-dicaffeoylquinic acid and 4,5-dicaffeoylquinic acid.

[58] The chlorogenic acids, the coffee bean extract or the oral composition according to any one of [49] to [57], wherein the oral composition is preferably a liquid composition comprising from 0.001 to 7% by mass, from 0.001 to 3% by mass, from 0.001 to 1.5% by mass, from 0.005 to 7% by mass, from 0.005 to 3% by mass, from 0.005 to 1.5% by mass, from 0.02 to 7% by mass, from 0.02 to 3% by mass or from 0.02 to 1.5% by mass of the chlorogenic acids in a total mass, or a solid composition comprising from 0.01 to 70% by mass, from 0.01 to 65% by mass, from 0.01 to 60% by mass, from 0.05 to 70% by mass, from 0.05 to 65% by mass, from 0.05 to 60% by mass, from 0.2 to 70% by mass, from 0.2 to 65% by mass or from 0.2 to 60% by mass of the chlorogenic acids in a total mass.

[59] The chlorogenic acids, the coffee bean extract or the oral composition according to any one of [49] to [58], wherein an amount of the oral composition administered or ingested per adult per day is preferably from 50 to 1,500 mg, from 70 to 1,500 mg, from 100 to 1,500 mg, from 50 to 1,000 mg, from 70 to 1,000 mg, from 100 to 1,000 mg, from 50 to 500 mg, from 70 to 500 mg or from 100 to 500 mg as an amount of the chlorogenic acids.

[60] The chlorogenic acids, the coffee bean extract or the oral composition according to any one of [49] to [59], wherein the oral composition is preferably administered or ingested for one week or more, more preferably two weeks or more, further preferably four weeks or more.

[61] The chlorogenic acids, the coffee bean extract or the oral composition according to any one of [49] to [60], wherein the oral composition is preferably administered or ingested during the period from after dinner until bedtime.

[62] The chlorogenic acids, the coffee bean extract or the oral composition according to any one of [49] to [61], wherein the oral composition is preferably administered or ingested within 1 hour before bedtime.

[63] The chlorogenic acids, the coffee bean extract or the oral composition according to any one of [49] to [62], wherein the climacteric symptom is preferably hot flash.

[64] A method for improving climacteric symptom, comprising orally administering chlorogenic acids to a subject.

[65] A method for improving climacteric symptom, comprising orally administering a coffee bean extract which comprises chlorogenic acids and in which a mass ratio of caffeine/chlorogenic acids is 0.015 or less, to a subject.

[66] The method according to [65], wherein the coffee bean extract is preferably a green coffee bean extract and/or a lightly roasted coffee bean extract.

[67] The method according to [65] or [66], wherein the mass ratio of caffeine/chlorogenic acids is preferably 0.014 or less, more preferably 0.010 or less, further preferably 0.0066 or less, further preferably 0.0050 or less, further preferably 0.0020 or less, further preferably 0.0005 or less.

[68] The method according to any one of [65] to [67], preferably comprising orally administering a liquid composition comprising 0.01% by mass or more and 10% by mass or less of the coffee bean extract in terms of solid content, or a solid composition comprising 0.1% by mass or more and 95% by mass or less of the coffee bean extract in terms of solid content, to the subject.

[69] The method according to any one of [65] to [68], wherein a content of caffeine in the coffee bean extract is preferably 0.5% by mass or less, more preferably 0.4% by mass or less, further preferably 0.3% by mass or less, further preferably 0.2% by mass or less, further preferably 0.15% by mass or less, further preferably 0.1% by mass or less, further preferably 0.05% by mass or less.

[70] The method according to any one of [64] to [69], wherein the chlorogenic acids is preferably at least one selected from the group consisting of 3-caffeoylquinic acid, 4-caffeoylquinic acid, 5-caffeoylquinic acid, 3-feruloylquinic acid, 4-feruloylquinic acid, 5-feruloylquinic acid, 3,4-dicaffeoylquinic acid, 3,5-dicaffeoylquinic acid and 4,5-dicaffeoylquinic acid, more preferably at least one selected from the group consisting of 3-caffeoylquinic acid, 4-caffeoylquinic acid, 5-caffeoylquinic acid, 3-feruloylquinic acid, 4-feruloylquinic acid and 5-feruloylquinic acid, further preferably at least one selected from the group consisting of 3-caffeoylquinic acid, 4-caffeoylquinic acid and 5-caffeoylquinic acid, more further preferably 3-caffeoylquinic acid, 4-caffeoylquinic acid and 5-caffeoylquinic acid, more further preferably 3-caffeoylquinic acid, 4-caffeoylquinic acid, 5-caffeoylquinic acid, 3-feruloylquinic acid, 4-feruloylquinic acid and 5-feruloylquinic acid, more further preferably 3-caffeoylquinic acid, 4-caffeoylquinic acid, 5-caffeoylquinic acid, 3-feruloylquinic acid, 4-feruloylquinic acid, 5-feruloylquinic acid, 3,4-dicaffeoylquinic acid, 3,5-dicaffeoylquinic acid and 4,5-dicaffeoylquinic acid.

[71] The method according to any one of [64] to [70], preferably comprising orally administering a liquid composition comprising 0.001% by mass or more and 7% by mass or less of the chlorogenic acids in a total mass, or a solid composition comprising 0.01% by mass or more and 70% by mass or less of the chlorogenic acids in a total mass, to the subject.

[72] The method according to any one of [64] to [71], preferably comprising orally administering from 50 to 1500 mg per adult per day of the chlorogenic acids.

[73] The method according to any one of [64] to [72], preferably comprising orally administering the chlorogenic acids for one week or more, more preferably two weeks or more, further preferably four weeks or more.

[74] The method according to any one of [64] to [73], preferably comprising administering the chlorogenic acids during the period from after dinner until bedtime, more preferably within 1 hour before bedtime.

[75] The method according to any one of [64] to [74], wherein the climacteric symptom is preferably hot flash.

[76] The method according to any one of [64] to [75], wherein the subject is preferably a climacteric human, more preferably a climacteric female, further preferably a climacteric female having a symptom of hot flash, further preferably a climacteric female having a symptom of hot flash twice or more a week on average, further preferably a climacteric female having a symptom of hot flash four times or more a week on average, further preferably a climacteric female having a symptom of hot flash seven times or more a week on average.

EXAMPLES

Hereinafter, the present invention will be more specifically described based on Examples, but the present invention is not limited thereto.

Reference Example 1

(1) Measurement of Chlorogenic Acids
[Analytical Instrument]
HPLC was used.
Apparatus: Waters ACQUITY UPLC-H Class PDA
Separation column: ACQITY UPLC HSS C18 2.1×100 mm, 1.8 μm Detector (ultraviolet-visible absorptiometer): L-2420
[Analysis Conditions]
Amount of sample injected: 10 μL,
Flow rate: 1.0 mL/min,
Detection wavelength of ultraviolet absorptiometer: 325 nm
Eluent A: 5% (v/v) acetonitrile containing 0.05 mol/L acetic acid, 0.01 mol/L sodium acetate and 0.1 mmol/L HEDPO (1-hydroxyethane-1,1-diphosphonic acid)
Eluent B: acetonitrile
[Concentration Gradient Conditions]

| Time (min) | Liquid A (% (v/v)) | Liquid B (% (v/v)) |
|---|---|---|
| 0 | 100 | 0 |
| 2.5 | 100 | 0 |
| 3.5 | 95 | 5 |
| 5.0 | 95 | 5 |
| 6.0 | 92 | 8 |
| 16.0 | 92 | 8 |
| 16.5 | 10 | 90 |
| 19 | 100 | 0 |
| 22 | 100 | 0 |

[Retention Time of Chlorogenic Acids]
3-Caffeoylquinic acid (3-CQA): 5.2 min
5-Caffeoylquinic acid (5-CQA): 8.7 min
4-Caffeoylquinic acid (4-CQA): 11.2 min
3-Feruloylquinic acid (3-FQA): 12.6 min
5-Feruloylquinic acid (5-FQA): 19.1 min
4-Feruloylquinic acid (4-FQA): 20.9 min
3,5-Dicaffeoylquinic acid (3,5-di-CQA): 37.0 min
4,5-Dicaffeoylquinic acid (4,5-di-CQA): 37.5 min
3,4-Dicaffeoylquinic acid (3,4-di-CQA): 44.8 min 5-CQA was adopted as a standard substance, according to the area percentages determined, and the amount of the chlorogenic acids was quantitatively determined as the total of such nine compounds.

(2) Measurement of Caffeine

Reagent caffeine was adopted as a standard substance, and measurement of caffeine was made with an absorbance at a wavelength of 270 nm, in the same manner as in (1) above. The amount of caffeine was quantitatively determined from the area ratio determined from the peak area at 5.2 minutes.

Test Example 1

(1) Production of Green Coffee Bean Extract

Five hundred g of a green Indonesian Robusta AP-1 bean was stirred and extracted in 5 L of hot water at 98° C. for 4 hours. After cooling, solid-liquid separation was performed, and an extraction liquid was concentrated under reduced pressure at 40° C. until the solid content concentration reached 20 w/v %, thereby providing a coarse green coffee bean extract.

Ethanol was slowly added to the coarse green coffee bean extract having a solid content concentration of 20 w/v %, the concentration of the ethanol was then adjusted to 60 w/v %, 63 g of acid earth (Mizuka-Ace #600, manufactured by Mizusawa Industrial Chemicals Ltd.) was then added, and the resultant was then stirred for 2 hours and thereafter filtered by #2 filter paper.

Next, the resultant was allowed to pass through a column filled with 125 g of activated carbon (Kuraray Coal GW48/100D, manufactured by Kuraray Co., Ltd.) and a column filled with 32 mL of an H-type cation exchange resin (SK1BH, manufactured by Mitsubishi Chemical Corporation), and then again filtered by a 0.2-μm membrane filter.

Ethanol in the filtrate was distilled off at 40° C. and the water content was then adjusted for adjustment of the solid content to 40 w/v %, and the resultant was defined as "liquid where the concentration of the chlorogenic acids was adjusted". Ten g of the "liquid where the concentration of the chlorogenic acids was adjusted" was sampled in a centrifuge tube, and then centrifuged in condition of 3,000 r/min, 15° C. and 60 minutes, and the supernatant was defined as "purified green coffee bean extract".

The contents of the chlorogenic acids and caffeine in the purified green coffee bean extract obtained were as follows based on the total amount of the purified green coffee bean extract and the solvent thereof: a content of monocaffeoylquinic acid (CQA) of 13.01% by mass, a content of monoferuloylquinic acid (FQA) of 2.62% by mass, a content of dicaffeoylquinic acid (di-CQA) of 3.72% by mass, and a content of caffeine of 0.008% by mass. The amount of the chlorogenic acids (CQA+FQA+di-CQA) and the content of caffeine, based on the solid content of the purified green coffee bean extract, were 49.8% by mass and 0.02% by mass, respectively. The mass ratio of caffeine/chlorogenic acids (CQA+FQA+di-CQA) in the purified green coffee bean extract was 0.0004.

(2) Production of Test Drink

The purified green coffee bean extract produced in (1) above was used to prepare a test drink (containing chlorogenic acids (CQA+FQA+di-CQA) at a rate of 330 mg/100 mL) and a placebo drink (containing chlorogenic acids (CQA+FQA+di-CQA) at a rate of 0 mg/100 mL), according to the formulation table in Table 1.

TABLE 1

| (% by mass) | Test drink | Placebo drink |
|---|---|---|
| Purified green coffee bean extract | 2 | — |
| Sweetener | 3 | 3 |
| Acidulant | 0.8 | 0.8 |
| Flavor modifier | 0.8 | 0.8 |
| Dextrin | 2 | 2 |
| Ion-exchange water | Balance | Balance |
| Total | 100.0 | 100.0 |
| Chlorogenic acids (mg/100 mL) | 330 | 0 |

(3) Test Overview
[Test Subject and Test Method]

Sixty-two females (from 46 to 58 years old) were divided to two groups in a balanced manner in terms of the age, the height, the weight, BMI and the blood pressure. One group was defined as chlorogenic acids group (31 females, 51.5±3.1 years old), and another group was defined as a placebo group (31 females, 51.6±3.3 years old). A test drink comprising chlorogenic acids and a placebo drink comprising no chlorogenic acids were ingested by the chlorogenic acids group and the placebo group, respectively, before bedtime by one bottle per day (100 mL) daily for two weeks.

[Evaluation of Climacteric Symptom]

Evaluation of climacteric symptom of each test subject was performed by a physical condition questionnaire according to VAS and a simplified menopausal index (SMI) (see, Takao KOYAMA and Takeshi ASO, Recent Progress of Kampo Medicine in Obstetrics and Gynecology. 1992; 9: 30-34) shown in Table 2. Such evaluation was performed on a weekly basis from the start of the test (week 0) to the end of the test (week 2). The number of hot flashes was recorded by each test subject daily for two weeks during the test.

TABLE 2

Simplified menopausal index (SMI)

| Symptom | Severe | Moderate | Mild | None |
|---|---|---|---|---|
| <1> Hot flush | 10 | 6 | 3 | 0 |
| <2> Perspiration | 10 | 6 | 3 | 0 |
| <3> Chilliness | 14 | 9 | 5 | 0 |
| <4> Irregular heartbeat | 12 | 8 | 4 | 0 |
| <5> Insomnia | 14 | 9 | 5 | 0 |
| <6> Irritability | 12 | 8 | 4 | 0 |
| <7> Depressed Mood | 7 | 5 | 3 | 0 |
| <8> Headache/Dizziness | 7 | 5 | 3 | 0 |
| <9> Tiredness | 7 | 4 | 2 | 0 |
| <10> Aching Joints/Muscles | 7 | 5 | 3 | 0 |

(i) Physical Condition Questionnaire According to VAS

Evaluation items were "flushing/flush (hot flash)", "sweating", "coldness", and "insomnia". A mark was made on a 100-mm straight line with respect to each of the evaluation items, by each test subject, under the assumption that the best condition and the worst condition with respect to each of the evaluation items, on an empirical basis in the past, corresponded to a light end (numerical value 0) and a right end (numerical value 100), respectively. The VAS value of each test subject (minimum 0, maximum 100) was determined based on the position of the mark. A higher VAS value means severer symptom. Test subjects with a VAS value of from 50 to 100 at week 0, with respect to "flushing/flush (hot flash)" and "insomnia", were selected from among 31 females in each of the groups. Test subjects with a VAS value of from 1 to 49 at week 0, with respect to "sweating", were selected therefrom. The VAS values at week 0, week 1 and week 2 were aggregated with respect to the test subjects selected. The values aggregated were subjected to a significant difference test between the placebo group and the chlorogenic acids group (Student's t-test).

(ii) Subjective Evaluation According to SMI

Each test subject selected one from the group consisting of "severe/moderate/mild/none" with respect to the symptom intensity of each of ten symptoms defined in SMI (Table 2) once per week. The symptom intensity was scored according to Table 2, and the average value between test subjects was aggregated with respect to each of the symptoms. The values aggregated were subjected to a significant difference test between the placebo group and the chlorogenic acids group (Student's t-test).

(iii) Number of Hot Flashes

The number of hot flashes was recorded by each test subject daily for two weeks during the test. The values recorded for two weeks were subjected to a significant difference test (ANOVA) between the placebo group and the chlorogenic acids group.

(4) Statistics and Results

Table 3 shows the results of the physical condition questionnaire according to VAS ((A) flushing/flush (hot flash), (B) sweating, and (C) insomnia). Table 4 shows the results of the subjective evaluation of each of the 31 females in each of the groups, according to SMI ((1) hot flush (2) perspiration (3) insomnia. Furthermore, FIG. 1 illustrates the change in the number of hot flashes per day in the 31 females in each of the groups during the testing period. The numerical values in the Tables and the FIGURE each indicate average value±standard error.

TABLE 3

(A) Flushing/flush (hot flash)

| | Week 0 | Week 1 | Week 2 |
|---|---|---|---|
| Placebo group (n = 19) | 70 ± 3 | 53 ± 5 | 44 ± 6 |
| Chlorogenic acids group (n = 12) | 72 ± 3 | 35 ± 7* | 26 ± 7* |

*There is significant difference within significance level of 5% relative to placebo group.

(B) Sweating

| | Week 0 | Week 1 | Week 2 |
|---|---|---|---|
| Placebo group (n = 14) | 25 ± 3 | 32 ± 6 | 33 ± 7 |
| Chlorogenic acids group (n = 14) | 21 ± 4 | 19 ± 5# | 11 ± 2** |

There is significant difference trend within significance level of 10% relative to placebo group.
**There is significant difference within significance level of 1% relative to placebo group.

(C) Insomnia

| | Week 0 | Week 1 | Week 2 |
|---|---|---|---|
| Placebo group (n = 22) | 67 ± 3 | 59 ± 4 | 56 ± 4 |
| Chlorogenic acids group (n = 21) | 67 ± 2 | 50 ± 4 | 46 ± 4# |

There is significant difference trend within significance level of 10% relative to placebo group.

TABLE 4

(1) Hot flush

| | Week 0 | Week 1 | Week 2 |
|---|---|---|---|
| Placebo group | 5.2 ± 0.5 | 4.7 ± 0.4 | 4.0 ± 0.5 |
| Chlorogenic acids group | 4.4 ± 0.5 | 3.7 ± 0.3* | 2.7 ± 0.4* |

*There is significant difference within significance level of 5% relative to placebo group.

(2) Perspiration

| | Week 0 | Week 1 | Week 2 |
|---|---|---|---|
| Placebo group | 5.9 ± 0.5 | 4.9 ± 0.4 | 4.0 ± 0.5 |
| Chlorogenic acids group | 5.4 ± 0.5 | 4.5 ± 0.5 | 3.4 ± 0.5 |

(3) insomnia

| | Week 0 | Week 1 | Week 2 |
|---|---|---|---|
| Placebo group | 9.3 ± 0.7 | 8.2 ± 0.7 | 6.8 ± 0.7 |
| Chlorogenic acids group | 8.5 ± 0.7 | 7.3 ± 0.6 | 5.7 ± 0.7 |

From Table 3 and Table 4, any statistically significant improvement effect was observed in the chlorogenic acids group with respect to the items of "flushing/flush (hot flash)" and "hot flush", as compared with the placebo group. In addition, any statistically significant improvement or improvement trend was also observed with respect to the items of "sweating" and "perspiration and the items of "insomnia" and "insomnia". As illustrated in FIG. 1, the number of hot flashes per day in the chlorogenic acids group was changed on the decrease, as compared with the placebo group, during the testing period, and was significantly different from the placebo group. It was confirmed from the foregoing that hot flash as one climacteric symptom, and other symptoms were improved by ingestion of the coffee bean extract comprising the chlorogenic acids.

The invention claimed is:

1. A method for improving hot flash, comprising orally administering a coffee bean extract to a subject in need thereof, wherein the subject is a climacteric female having a symptom of hot flash, wherein the coffee bean extract comprises at least one chlorogenic acid, and a mass ratio of caffeine to the at least one chlorogenic acid in the coffee bean extract is 0.015 or less, and wherein from 100 to 500 mg per adult per day of the at least one chlorogenic acid is orally administered.

2. The method according to claim 1, wherein the coffee bean extract is a green coffee bean extract, a lightly roasted coffee bean extract or a combination thereof.

3. The method according to claim 1, wherein a content of caffeine in the coffee bean extract is 0.5% by mass or less.

4. The method according to claim 1, wherein the at least one chlorogenic acid is at least one selected from the group consisting of 3-caffeoylquinic acid, 4-caffeoylquinic acid, 5-caffeoylquinic acid, 3-feruloylquinic acid, 4-feruloylquinic acid, 5-feruloylquinic acid, 3,4-dicaffeoylquinic acid, 3,5-dicaffeoylquinic acid and 4,5-dicaffeoylquinic acid.

5. The method according to claim 1, wherein the coffee bean extract is administered for at least one week.

6. The method according to claim 1, wherein the coffee bean extract is administered during a period from after dinner until bedtime.

\* \* \* \* \*